(12) United States Patent
Mangiardi et al.

(10) Patent No.: US 8,986,360 B2
(45) Date of Patent: *Mar. 24, 2015

(54) DELIVERY DEVICE WITH SHORTENED INNER TUBE AND ASSOCIATED METHOD

(75) Inventors: Eric K. Mangiardi, Charlotte, NC (US); Jason M. Reynolds, Charlotte, NC (US); Jeff Reuther, Charlotte, NC (US)

(73) Assignee: Merit Medical Systems, Inc., South Jordan, UT (US)

( * ) Notice: Subject to any disclaimer, the term of this patent is extended or adjusted under 35 U.S.C. 154(b) by 819 days.

This patent is subject to a terminal disclaimer.

(21) Appl. No.: 11/432,964

(22) Filed: May 12, 2006

(65) Prior Publication Data

US 2007/0043421 A1 Feb. 22, 2007

Related U.S. Application Data

(60) Provisional application No. 60/680,556, filed on May 13, 2005.

(51) Int. Cl.
*A61F 2/06* (2013.01)
*A61F 2/95* (2013.01)
(Continued)

(52) U.S. Cl.
CPC . *A61F 2/95* (2013.01); *A61F 2/966* (2013.01); *A61F 2250/0091* (2013.01); *A61M 2025/0004* (2013.01)
USPC ........................................................ 623/1.11

(58) Field of Classification Search
USPC ........ 623/1.11, 1.12, 1.23; 606/108, 194, 198
See application file for complete search history.

(56) References Cited

U.S. PATENT DOCUMENTS

| | | |
|---|---|---|
| 5,201,757 A | 4/1993 | Heyn et al. |
| 5,759,186 A | 6/1998 | Bachmann et al. |
| 5,824,041 A | 10/1998 | Lenker et al. |

(Continued)

FOREIGN PATENT DOCUMENTS

| | | |
|---|---|---|
| DE | 43 23 866 A1 | 1/1994 |
| EP | 0 364 420 A | 4/1990 |

(Continued)

OTHER PUBLICATIONS

PCT Notification of Transmittal of the International Search Report and the Written Opinion of the International Searching Authority, or the Declaration, mailed Aug. 28, 2006 for PCT/US2006/018811 (Filed May 12, 2006).

(Continued)

*Primary Examiner* — Darwin Erezo
*Assistant Examiner* — Martin T Ton
(74) *Attorney, Agent, or Firm* — Stoel Rives LLP

(57) ABSTRACT

A delivery device for positioning and deploying an implantable device within a lumen is provided. The device includes a longitudinal outer tube having proximal and distal ends, wherein the implantable device is positioned proximate to the distal end of the outer tube. The device also includes a longitudinal inner tube slidably disposed within the outer tube and having proximal and distal ends, wherein at least a portion of the distal end of the inner tube is configured to underlie at least a portion of a proximal end of the implantable device. The distal end of the inner tube is located proximally of the distal end of the outer tube to define a gap for accommodating at least a portion of the implantable device. A mechanism is coupled to the inner and/or outer tubes and is operable to deploy the implantable device within the lumen.

26 Claims, 4 Drawing Sheets

(51) Int. Cl.
*A61F 2/966* (2013.01)
*A61M 25/00* (2006.01)

(56) References Cited

U.S. PATENT DOCUMENTS

| | | | |
|---|---|---|---|
| 5,868,755 A | | 2/1999 | Kanner et al. |
| 5,954,729 A | | 9/1999 | Bachmann et al. |
| 6,143,021 A | * | 11/2000 | Staehle .................. 623/1.11 |
| 6,162,231 A | | 12/2000 | Mikus et al. |
| 6,391,051 B2 | | 5/2002 | Sullivan, III et al. |
| 6,413,269 B1 | * | 7/2002 | Bui et al. .................. 623/1.11 |
| 6,428,566 B1 | | 8/2002 | Holt |
| 6,514,261 B1 | | 2/2003 | Randall et al. |
| 6,629,981 B2 | * | 10/2003 | Bui et al. .................. 606/108 |
| 6,669,719 B2 | | 12/2003 | Wallace et al. |
| 6,726,712 B1 | * | 4/2004 | Raeder-Devens et al. ... 623/1.11 |
| 6,866,669 B2 | | 3/2005 | Buzzard et al. |
| 7,309,350 B2 | | 12/2007 | Landreville et al. |
| 7,393,357 B2 | | 7/2008 | Stelter et al. |
| 7,731,654 B2 | | 6/2010 | Mangiardi et al. |
| 8,439,934 B2 | | 5/2013 | Satasiya et al. |
| 8,518,099 B2 | | 8/2013 | Chanduszko et al. |
| 8,535,366 B2 | | 9/2013 | Mangiardi et al. |
| 2002/0151967 A1 | | 10/2002 | Mikus et al. |
| 2002/0183827 A1 | * | 12/2002 | Derus et al. .................. 623/1.12 |
| 2003/0050686 A1 | * | 3/2003 | Raeder-Devens et al. ... 623/1.11 |
| 2003/0167060 A1 | | 9/2003 | Buzzard et al. |
| 2004/0193243 A1 | * | 9/2004 | Mangiardi et al. ........... 623/1.11 |
| 2004/0267281 A1 | | 12/2004 | Harari et al. |
| 2005/0090887 A1 | | 4/2005 | Pryor |
| 2005/0125050 A1 | * | 6/2005 | Carter et al. .................. 623/1.11 |
| 2005/0149160 A1 | | 7/2005 | McFerran |
| 2005/0278010 A1 | | 12/2005 | Richardson |
| 2007/0100421 A1 | | 5/2007 | Griffin |
| 2007/0208350 A1 | | 9/2007 | Gunderson |
| 2007/0270932 A1 | | 11/2007 | Headley et al. |
| 2009/0099636 A1 | | 4/2009 | Chanduszko et al. |
| 2009/0118740 A1 | | 5/2009 | Mangiardi et al. |
| 2009/0192518 A1 | | 7/2009 | Golden et al. |
| 2010/0049295 A1 | | 2/2010 | Satasiya et al. |

FOREIGN PATENT DOCUMENTS

| | | |
|---|---|---|
| EP | 0 872 220 A1 | 10/1998 |
| WO | WO 96/31174 | 10/1996 |
| WO | WO 00/78246 | 12/2000 |
| WO | WO 02/087470 | 11/2002 |
| WO | WO 03/090644 | 11/2003 |
| WO | WO 2004/030571 | 4/2004 |
| WO | WO 2005/070095 | 8/2005 |
| WO | WO 2008/042266 | 4/2008 |
| WO | PCT/US2012/062603 | 10/2012 |

OTHER PUBLICATIONS

Office Action dated Jan. 22, 2013 for U.S. Appl. No. 10/585,430.
Office Action for U.S. Appl. No. 10/585,430 dated Aug. 13, 2012.
The Supplementary European Search Report for EP Application No. 05705271.4, dated May 4, 2007.
International Search Report and Written Opinion for PCT/US2009/052691 dated Oct. 29, 2009.
Office Action for U.S. Appl. No. 10/585,430 dated Dec. 8, 2009.
Office Action dated Jun. 7, 2011 for U.S. Appl. No. 10/585,430.
Restriction Requirement dated Mar. 6, 2012 for U.S. Appl. No. 12/535,980.
Office Action dated May 25, 2012 for U.S. Appl. No. 12/535,980.
Office Action dated Jan. 31, 2012 for U.S. Appl. No. 10/585,430.
Office Action for U.S. Appl. No. 10/585,430 dated Nov. 9, 2010.
Office Action dated Nov. 14, 2012 for U.S. Appl. No. 12/535,980.
International Publication and Search Report dated Feb. 25, 2012 for WO10021836.
International Publication and Search Report dated Aug. 4, 2005 for WO2005070095.
International Publication and Search Report dated Jun. 14, 2012 for WO2012078794.
U.S. Appl. No. 13/313,929, filed Oct. 30, 2012, Robinson.
U.S. Appl. No. 13/664,137, filed Oct. 30, 2012, Robinson.
U.S. Appl. No. 13/664,200, filed Oct. 30, 2012, Robinson.
U.S. Appl. No. 13/664,234, filed Oct. 30, 2012, Robinson.
U.S. Appl. No. 13/664,267, filed Oct. 30, 2012, Robinson.
Notice of Allowance dated Mar. 6, 2013 for U.S. Appl. No. 12/535,980.
International Search Report and Written Opinion dated Mar. 29, 2013 for PCT/US2012/062603.
Notice of Allowance dated Jun. 11, 2013 for U.S. Appl. No. 10/585,430.
Office Action dated May 5, 2014 for U.S. Appl. No. 13/313,929.
Notice of Allowance dated Oct. 21, 2014 for U.S. Appl. No. 13/313,929.

* cited by examiner

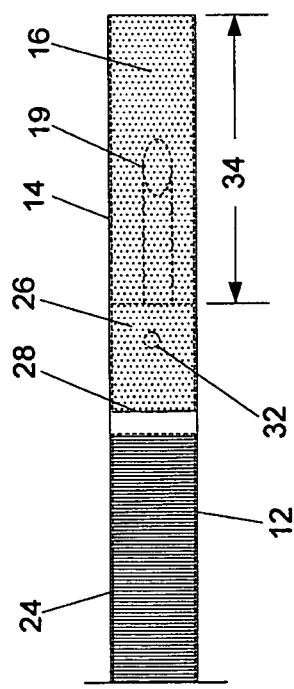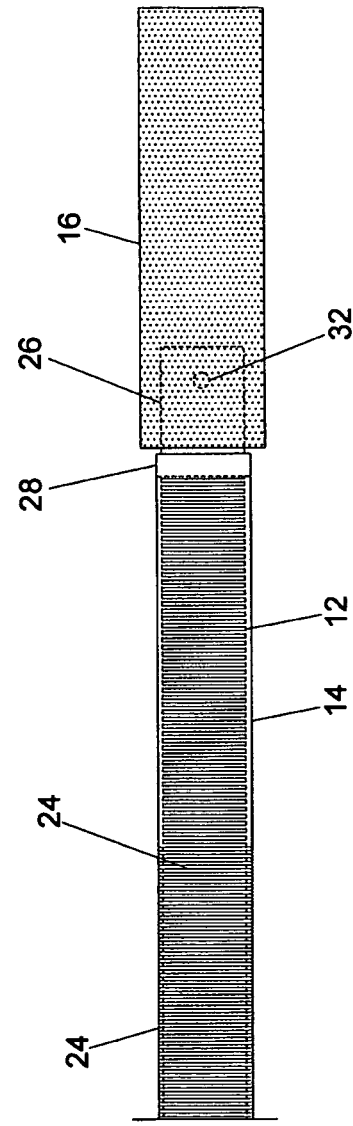

DELIVERY DEVICE WITH SHORTENED INNER TUBE AND ASSOCIATED METHOD

CROSS-REFERENCE TO RELATED APPLICATIONS

The present application claims priority U.S. Provisional Application No. 60/680,556 entitled "Delivery Device with Shortened Inner Tube and Associated Method," filed May 13, 2005, the contents of which are incorporated herein by reference.

BACKGROUND OF THE INVENTION

1) Field of the Invention

The present invention relates to a delivery device and, in more particular, to a delivery device that is capable of being positioned within a lumen and deploying an implantable device therein.

2) Description of Related Art

Stents are devices that are inserted into body lumina such as vessels or passages to keep the lumen open and prevent closure due to a stricture, external compression, or internal obstruction. In particular, stents are commonly used to keep blood vessels open in the coronary arteries, and they are frequently inserted into the ureters to maintain drainage from the kidneys, the bile duct for pancreatic cancer or cholangiocarcinoma, or the esophagus or airways for strictures or cancer. Vascular as well as nonvascular stenting has evolved significantly; unfortunately, there remain significant limitations with respect to effectively implanting the stents into a patient's lumen.

In order to serve its desired function, the stent should be delivered precisely and oriented correctly. Improper installation can lead to tissue luminal inflammation and tissue granulation. In order to facilitate the delivery of stents, delivery devices, such as endoscopes and catheters, have been utilized to deploy stents more precisely. Unfortunately, guidance of the stent has substantially remained a function of physician skill resulting from substantial practice. This fact has become particularly evident with the advent of radially expanding stents. The physician frequently needs to measure the length of the lesion, align a distal end of the of the delivery device, and rely on accurate deployment to ensure that the entire lesion is covered by the stent. Moreover, delivery devices typically do not give physicians adequate visual certainty that the device has been installed at the desired target site. Optical devices are typically employed at a distal end of the delivery device, which provides limited visibility of the entire lesion with respect to the stent. If after full deployment of the stent, the physician discovers the stent has been implanted incorrectly, there is no conventional way of correcting the error short of removing the stent.

Techniques have been developed to address the problem of increasing visibility of the lesion prior to deploying the stent. For example, U.S. Patent Application Publication No. 20040193243 to Mangiardi et al. which is assigned to the present assignee and incorporated herein by reference, discloses a medical appliance optical delivery and deployment apparatus. The apparatus includes an inner tubular member disposed within an outer tubular member, where the outer tubular member is typically shorter than the inner tubular member and movable relative to the inner tubular member. A distal region of the outer tubular member surrounds the stent and maintains the stent in a crimped delivery configuration, while a distal region of the inner tubular member is surrounded by the stent. The outer tubular member may be clear so that the inner tubular member and markers are visible therethrough. An optical guidewire may extend through the inner tubular member or utility channels defined in the outer tubular member to a distal tip, or the distal tip may be configured to have a light source and lens. In addition, the inner tubular member may include optical windows proximate to the distal tip that are preferably beveled and oval to facilitate viewing with an optical instrument. The optical windows may also be staggered along the inner tubular member to increase visualization proximate to the distal tip. Once properly positioned at a site of a lesion, the outer tubular member is retracted to deploy the stent and allow the stent to radially expand.

The inner and outer tubular members, optical instruments, and optical windows provide increased visualization of the lesion prior to deploying the stent. Despite these improvements, additional innovations in positioning an implantable device and visualizing a lesion and implantable device to promote more accurate delivery of the implantable device are also desired.

Therefore, there is a need in the industry for a delivery device that is capable of effectively and accurately positioning an implantable device within a patient's lumen. In addition, there is a need for a delivery device that is capable of increasing the visibility of the lumen and implantable device prior to and during deployment of the implantable device.

BRIEF SUMMARY OF THE INVENTION

The invention addresses the above needs and achieves other advantages by providing a delivery device for deploying an implantable device within a lumen. The delivery device includes an inner tube positioned within an outer tube, where the distal end of the inner tube is positioned proximally of the distal end of the outer tube to define a gap therebetween. An optical instrument, such as a camera, is capable of being positioned through the distal end of the inner tube and within the gap to view the implantable device and lumen proximate to a target area. As a result, the delivery device is capable of ensuring that the implantable device is properly positioned proximate to the target area of the lumen.

In one embodiment of the present invention, a delivery device for positioning and deploying an implantable device within a lumen and proximate to a target area is provided. The device includes a longitudinal outer tube having proximal and distal ends, wherein the implantable device is positioned proximate to the distal end of the outer tube. The device also includes a longitudinal inner tube slidably disposed within the outer tube and having proximal and distal ends, wherein at least a portion of the distal end of the inner tube is configured to underlie at least a portion of a proximal end of the implantable device. The distal end of the inner tube is located proximally of the distal end of the outer tube to define a gap for accommodating at least a portion of the implantable device. A mechanism is coupled to the inner and/or outer tubes and is operable to deploy the implantable device within the lumen. The mechanism could include at least one actuator coupled to the outer tube.

In various aspects of the delivery device, the device further includes an optical device positioned within the gap such that the optical device is capable of viewing at least a portion of the implantable device and/or target area prior to or during deployment of the implantable device. A side opening could be defined in each of the inner and outer tubes, wherein the outer tube is capable of sliding over the inner tube to substantially align each of the side openings with each other. An optical device could be positioned within the inner tube and proximate to each side opening such that the optical device is capable of viewing at least a portion of the target area when the side openings are aligned with each other.

In additional aspects of the delivery device, a coil is positioned within each of the inner and outer tubes. Each of the inner and outer tubes may include a semi-transparent polymeric material, such as polytetrafluoroethylene and/or polyether block amide. The device could also include a collar positioned on the inner tube, wherein a proximal end of the implantable device is positioned at least partially on the distal end of the inner tube and adjacent to the collar. The inner tube could include at least one anchor to engage at least a portion of the proximal end of the implantable device.

Furthermore, one aspect of the present invention provides a method for deploying an implantable device within a lumen proximate to a target area. The method includes positioning an inner tube within an outer tube such that a gap is defined between respective distal ends of each of the inner and outer tubes. The method also includes positioning the implantable device at least partially within the gap, and positioning the inner and outer tubes within the lumen. The method further includes deploying the implantable device with a mechanism proximate to the target area.

In aspects of the method, the method further includes positioning an optical device within the gap to view at least a portion of the implantable device and/or target area. The method includes positioning a proximal end of the implantable device at least partially on a distal end of the inner tube. In addition, the method includes positioning the implantable device over at least one anchor defined on the inner tube. Furthermore, the deploying step may include sliding the outer tube proximally over the inner tube with the mechanism. The method can also include moving the inner and outer tubes proximally within the lumen while the implantable device is positioned within the gap to reposition the implantable device.

BRIEF DESCRIPTION OF THE SEVERAL VIEWS OF THE DRAWINGS

Figure 1:
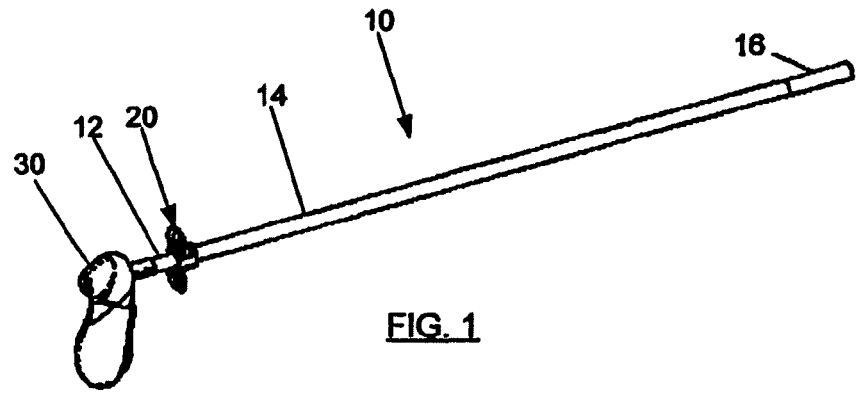
Figure 2A:
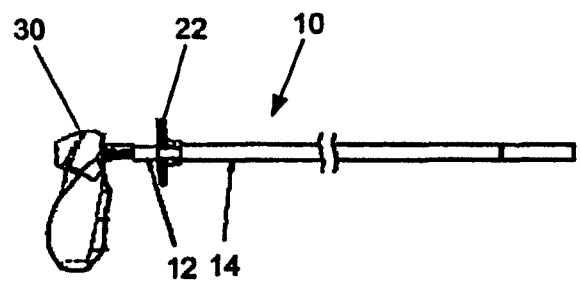
Figure 2B:
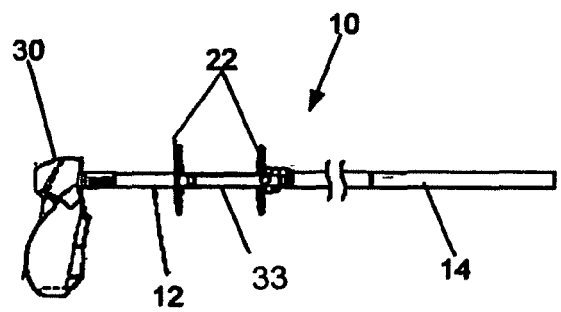
Figure 5:
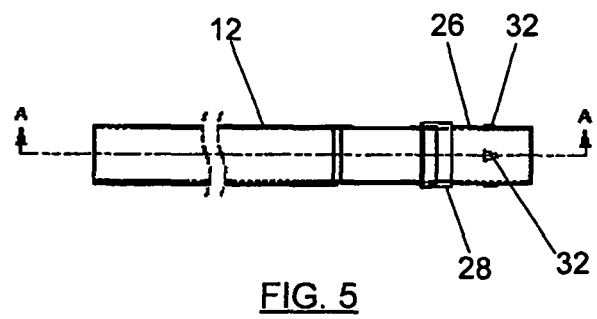
Figure 5A:
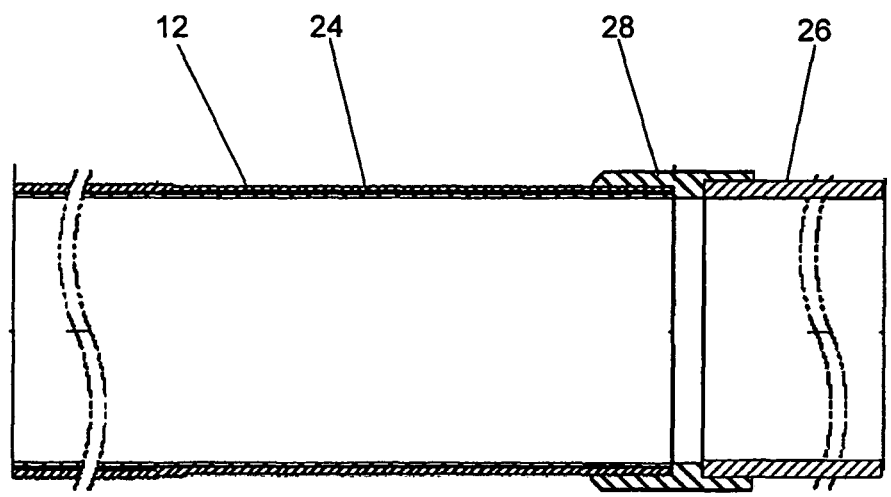

Having thus described the invention in general terms, reference will now be made to the accompanying drawings, which are not necessarily drawn to scale, and wherein:

FIG. 1 is a perspective view of a delivery device according to one embodiment of the present invention;

FIG. 2A is a side view of the delivery device shown in FIG. 1;

FIG. 2B is a side view of a delivery device according to another embodiment of the present invention;

FIG. 3 is a partial plan view of a delivery device having an implantable device contained therein, according to another embodiment of the present invention;

FIG. 4 is another partial plan view of the delivery device shown in FIG. 3, depicting the implantable device deployed from the delivery device;

FIG. 5 is an elevation view of an inner tube assembly according to another embodiment of the present invention; and FIG. 5A is a partial cross-sectional view taken through line A-A of the inner tube assembly shown in FIG. 5.

Figure 6:
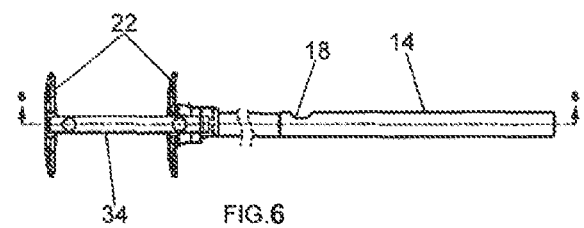
Figure 7:
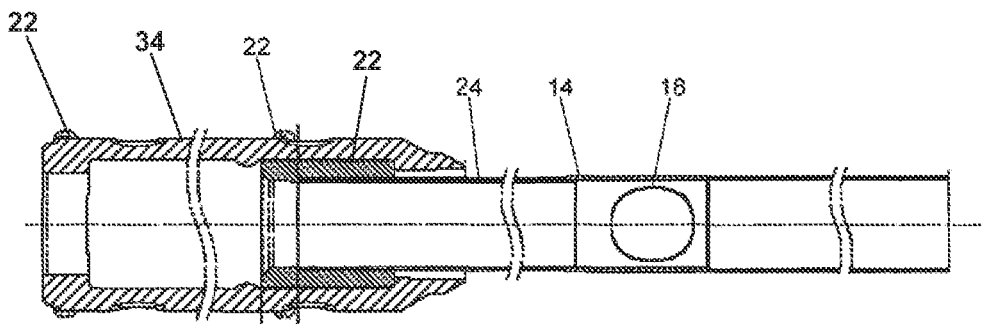

FIG. 6 is a side view of an additional outer tube assembly according to one embodiment of the present invention;

FIG. 7 is a partial cross-sectional view taken through line B-B of the outer tube assembly shown in FIG. 6.

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

With reference to FIG. 1, a delivery device 10 is shown. The delivery device 10 generally includes an inner tube 12 positioned within an outer tube 14 and capable of sliding therein. The delivery device 10 also includes a deployment mechanism 20 that is capable of deploying an implantable device 16 out of the distal end of the outer tube 14. The inner 12 and outer 14 tubes are configured to provide increased visibility of the target area and implantable device 16 to ensure that the implantable device 16 is properly aligned prior to deploying the implantable device within the lumen.

Thus, the delivery device 10 is capable of being deployed within a lumen proximate to a target area. "Target area," as used herein, is not meant to be limiting, as the target area could be a stricture, lesion, tumor, occlusion, fistulae, or other complication where the lumen passageway has been significantly reduced or compromised. The delivery device 10 is typically utilized to deploy the implantable device 16 within a lumen. However, the delivery device 10 is also capable of being used for surgical or endoscopic techniques to decrease the complexity of the procedure. For example, the delivery device 10 could be applicable to laparoscopy and arthrectomy.

It is understood that the delivery device 10 is applicable to a wide range of intraluminal applications. For example, the delivery device 10 could be used for implanting the implantable device 16 within lumina of the esophagus, trachea, arteries, or the biliary tract. The implantable device could be, for example, a stent, drug delivery device, or other medical device or drug known to those skilled in the art now or in the future. Furthermore, any number of configurations of implantable devices 16 could be incorporated and still be within the present scope of the invention. An exemplary embodiment of the interstice geometry of a stent and methods of manufacturing the stent is disclosed in U.S. Patent Publication No. 20040127973, entitled "Removable Biliary Stent," which is assigned to the present assignee and is incorporated herein by reference.

Both the inner tube 12 and outer tube 14 are typically flexible for positioning and maneuvering the tubes within a lumen. Each of the inner 12 and outer 14 tubes is also typically transparent or semi-transparent, such that the inner tube is visible through the outer tube. Moreover, the inner tube 12 may include markers for positioning and deploying the implantable device 16, although the inner and/or outer tubes could include markers if desired. For instance, the distal end of the outer tube 14 may include a marker to locate the distal end of the implantable device 16. The inner tube 12 is slightly smaller in diameter than the outer tube 14 such that the inner tube may slide within the outer tube.

However, the inner 12 and outer 14 tubes may be various sizes and configurations to accommodate a desired implantable device 16. For example, the inner 12 and outer 14 tubes could be about 6 to 10 mm in diameter and about 250-500 mm in length. Each of the inner 12 and outer 14 tubes could also be various diameters and wall thicknesses along the length of each tube for varying flexibility and/or aiding in securing or deploying the implantable device 16.

A substantial portion of each of the inner 12 and outer tubes 14 includes an assembly of polymeric materials. For instance, the polymeric materials could be a polytetrafluoroethylene ("PTFE"), such as Teflon® (E.I. DuPont de Nemours and Co. Corp.), and a polyether block amide ("PEBA"), such as Pebax® (Atofina Corp.). In addition, the inner 12 and outer 14 tubes also typically include a metal coil 24. More specifically, when constructing the inner 12 and outer 14 tubes, a PTFE liner is placed over a mandrel, and a coil 24 is wound around the PTFE liner while positioned on the mandrel. The PEBA material is configured as a tube and slid over the wound coil 24 and the PTFE liner while the assembly is supported on the mandrel. The assembly is then heated such that the PEBA outer sheath and the PTFE liner are adhered together over the coil to form a tube assembly. The PTFE liner is typically etched so that the PEBA material attaches or fuses to the PTFE material. During the etching process, the PTFE liner is typically discolored from a clear color to a yellowish brown. The remaining portions of the inner 12 and outer 14 tubes (i.e., the distal portions of the tubes where no coil is present) are typically a combination of PTFE and PEBA materials. The interior of the inner 12 and outer 14 tubes are thus a low-friction PTFE material, which allows various devices and instruments to slide therethrough and requires lower deployment forces when retracting the outer tube 14 during deployment of the implantable device 16. The inner tube 12 is fixedly attached at its proximal end adjacent to a handle 30. Thus, the proximal end of the inner tube 12 may be molded or otherwise attached to a portion of the handle 30, such as with an adhesive.

Each coil 24 extends from a proximal end of the each of the inner 12 and outer 14 tubes and substantially along the length of respective inner and outer tubes. In particular, the coil 24 within the inner tube 12 extends proximal to the distal end of the inner tube, while the coil within the outer tube 14 ends proximally of the distal end of the outer tube. Rather, the coil 24 within the outer tube 14 substantially aligns with the coil within the inner tube 12 prior to deploying the implantable device such that the portion of the outer tube 14 located distally of the coil includes only polymeric material. The coils 24 maintain a desired flexibility for the inner 12 and outer 14 tubes, but also preventing kinking or buckling when manipulating the inner and outer tubes within the lumen.

It is understood that the coil 24 could extend various lengths along each of the inner 12 and outer 14 tubes for imparting various amounts of flexibility and visibility within a gap 34, as will be explained in further detail below. Thus, the coil 24 could extend to the distal end of each of the inner 12 and outer 14 tubes, or the coil could end proximally of respective distal ends.

The deployment mechanism 20 typically includes one or more actuators 22 attached to the outer tube 14. The number of actuators 22 can be varied depending on the length of the implantable device 16. For example, there could be one actuator 22 for shorter implantable devices (e.g., 20-60 mm), as depicted in FIG. 2A, and two or more actuators for longer implantable devices (e.g., 80 mm), as shown in FIG. 2B. When utilizing two or more actuators 22, the actuators may be operatively connected such that the actuators cooperate to deploy the implantable device 16. For example, FIG. 2B illustrates that a pair of actuators 22 are connected to one another with a connector 33, where one actuator deploys the implantable device 16 partially, while the second actuator deploys the implantable device the remaining distance. In particular, the connector 33 includes an aperture defined therein, where the proximal actuator 22 abuts the connector 33 and is capable of moving the connector 33 and outer tube 14 proximally until the connector 33 abuts the handle 30. In addition, the distal actuator 22 may slide proximally within the aperture to completely deploy the implantable device 16.

This arrangement of actuators 22 allows users of the delivery device 10 to deploy the implantable device 16 with one hand if desired. For example, with reference to FIGS. 1 and 2A-B, a user would place a palm of the hand on the handle 30 of the delivery device 10 and extend his or her fingers of the same hand to pull proximally on the actuators 22 in succession. The outer tube 14 is coupled to the actuators 22 such that movement of the actuators causes concurrent sliding of the inner tube 12 within the outer tube 16. More specifically, the proximal end of the outer tube 14 is attached to an actuator 22 such that moving the actuator proximally causes the outer tube 14 to slide proximally over the inner tube 12, while the inner tube remains stationary.

The deployment mechanism typically includes one or more actuators 22 attached to the outer tube 14. Depending on the length of the implantable device, there could be one actuator 22 for shorter implantable devices (e.g., 20-60 mm), as depicted in FIG. 2A, and two or more actuators for longer implantable devices (e.g., 80 mm), as shown in FIGS. 2B, 6, and 7. When utilizing two or more actuators 22, the actuators may be operatively connected such that the actuators cooperate to deploy the implantable device. For example, FIG. 6 illustrates that a pair of actuators 22 are connected to one another with a connector 34, where one actuator deploys the implantable device partially, while the second actuator deploys the implantable device the remaining distance. The connector 34 is configured such that moving the proximal actuator 22 proximally also causes the distal actuator to move proximally. In addition, the distal actuator 22 may slide within the connector 34 proximally to completely deploy the implantable device.

It is understood that various techniques could be employed to deploy the implantable device 16. As such, the deployment mechanism 20 could be a device or an actuator capable of deploying the implantable device 16 distally out of the outer tube 14. For example, the actuators 22 could be configured to slide the inner tube 12 distally within the outer tube 14 such that the outer tube remains stationary. Moreover, the mechanism 20 could be various sizes and configurations. For instance, although the actuators 22 are T-shaped, the actuators could be configured as a trigger to grip the actuator.

As shown in FIGS. 5 and 5A, a collar 28 is positioned on the inner tube 12 to define a distal portion 26 between a distal edge of the collar and the distal edge of the inner tube. The distal portion 26 underlies a proximal end of the implantable device 16 when deploying the implantable device. The collar 28 is slightly larger in diameter than the inner tube 12 and is positioned on the inner tube such that the inner tube and collar are operatively connected. Typically, the diameter of the collar 28 and the implantable device 16 are approximately the same when the outer tube 14 is positioned over the collar and implantable device.

A proximal end of the implantable device 16 extends partially over the distal portion 26. In particular, the proximal end of the implantable device 16 is positioned on the distal portion 26 and adjacent to the collar 28, as shown in FIG. 3, and the collar can be colored or include a marker for identifying the proximal end of the implantable device within the lumen. In addition, the inner tube 12 may include anchors 32 that extend outwardly therefrom at spaced intervals about the circumference of the distal portion 26. The anchors 32 could be barbs, bumps, rings, protuberances, or the like that prevent the implantable device 16 from compressing along its length during deployment of the device. Moreover, the anchors 32 can provide frictional engagement between the inner tube 12, implantable device 16, and outer tube 14, or engage openings defined in the implantable device. The distal portion 26 and anchors 32 are also capable of engaging the implantable device 16 so as to allow repositioning of the delivery device 10 or the implantable device when the implantable device is partially deployed. For example, after partially deploying the implantable device 16, the delivery device 10 could be moved proximally to reposition the implantable device within the lumen. Thus, the distal portion 26 and anchors 32 prevent the implantable device 16 from deploying further during repositioning.

It is understood that the distal portion 26 shown and described above may be various sizes and configurations in alternative embodiments of the present invention. For instance, the distal portion 26 could be a separate component (e.g., pusher) of the inner tube such that the distal portion is not integrally formed with the inner tube. In addition, the collar 28 could be integrally formed with the inner tube 12 or configured to couple the inner tube and a separate distal portion 26. Generally, the inner tube 12 and collar 28 remain stationary while the outer tube 14 is retracted. However, the inner tube 12 and collar 28 may be configured to advance the implantable device 16 such that the inner tube 12 may be moved distally while the outer tube 14 remains stationary or is moved concurrently in a proximal direction.

With reference to FIG. 3, the distal end of the inner tube 12 does not extend to the distal end of the outer tube 14. As such, a gap 34 is defined between the distal ends of each of the inner 12 and outer 14 tubes, where the gap is capable of accommodating the implantable device 16. Thus, the gap 34 could be approximately the same length as the implantable device 16. A substantial portion of the implantable device 16 is positioned adjacent to the interior of the outer tube 14, while only a portion of the inner tube 12 or distal portion 26 extends within the interior of the implantable device. Accordingly, because the inner tube 12 is positioned proximally of the distal end of the outer tube 14, the gap 34 allows an optical device 19 to directly view the implantable device 16 for defects or positioning prior to or during deployment, such as inspecting for bent struts or a torn cover. In addition, the optical device 19 is also capable of viewing the target area through the outer tube while located within the gap 34 before, during, and after deployment. Thus, the optical device 19 is capable of viewing the target area and implantable device 16 to ensure that the implantable device is properly positioned. As described above, the coil 24 within the outer tube 14 typically does not extend to the distal end of the outer tube, which also provides increased visibility through the outer tube.

The gap 34 also allows an optical device 19 to inspect the position and/or orientation of the implantable device prior to deployment. For instance, the implantable device 16 could be a drug-eluting stent that includes a portion that is designated for drug delivery. Thus, the optical device 19 could be positioned within the gap 34 and employed to view the drug-eluting stent to ensure that the drug delivery portion is properly oriented with the target area that is to be treated. The drug-delivery portion could be colored or include markers so that various imaging techniques may be used to orient the drug-eluting stent either proximally/distally or rotationally within the lumen.

The gap 34 could be various sizes and configurations to accommodate a particular implantable device 16. Furthermore, an optical, surgical, or other instrument known to those skilled in the art may be utilized to access the gap 34 and/or distal end of the outer tube 14. Thus, the instrument could extend through the distal ends of the inner 12 and outer 14 tubes. Furthermore, it is understood that although the instrument is typically placed within the lumen of the inner tube, the inner tube could include one or more utility channels positioned therein for accommodating various instruments. In addition, the inner 12 and outer 14 tubes can further include aligned side openings defined in each of the tubes so that the optical device can be positioned to also view the target area through the side openings, as discussed in more detail in U.S. patent application Ser. No. 11/128,509, entitled "Delivery Device with Viewing Window and Associated Method," which is assigned to the assignee of the present invention and incorporated herein by reference. Furthermore, the inner 12 may include a side opening defined therein, while the outer tube 14 may be comprised of a transparent or semi-transparent material, such that an optical instrument is capable of viewing the target area through the side opening and the transparent or semi-transparent outer tube.

The implantable device 16 is deployed within a lumen and proximate to a target area using techniques known to those skilled in the art. For instance, the implantable device may be introduced orally with the delivery device 10, through the lumen, and proximate to a target area. The implantable device 16 is typically contracted to a smaller first diameter from a relaxed position. Once contracted, the implantable device 16 is positioned within the outer tube 14 of the delivery device proximate to the distal end of the outer tube. The inner tube 12 is positioned within the outer tube 14 such that the distal end of the inner tube is positioned proximate to the proximal end of the implantable device 16. A portion of the implantable device 16 may be positioned at the distal end of the inner tube 12 to engage the anchors 32. Prior to deployment, the implantable device 16 is positioned within the gap 34 defined between the distal portion 26 and the distal end of the outer tube 14.

An optical device 19 is positioned within the gap 34 and proximate to the target area and/or implantable device such that the optical device is capable of viewing at least a portion of the target area through the outer tube 14. In addition, the optical instrument could be used to inspect the implantable device 16 prior to deployment. The implantable device 16 is positioned proximate to the target area such that when the implantable device is deployed from the outer tube 14, the implantable device, if formed from an expansible material, can expand to receive the target area and even expand the diameter of the target area. In particular, the distal end of the outer tube 14 is positioned proximate to a distal end of the target area. The outer tube 14 is then retracted over the inner tube 12 using one or more actuators 22, while the distal portion 26 and collar 28 support the proximal end of the implantable device 16. The implantable device 16 is typically deployed incrementally along its length so that a more controlled deployment and accurate position is achieved. FIG. 4 shows the implantable device 16 in a deployed and expanded state, where the collar 28 is positioned proximate to a distal end of the outer tube 14.

The present invention includes several advantages. For instance, the gap 34 of the delivery device 10 facilitates increased visibility proximate to the target area. In particular, the optical device 19 is able to view the target area and/or implantable device 16 to ensure that the implantable device will be deployed to cover the entire target area. Because the implantable device 16 is more accurately positioned within the lumen, the probability of misalignment and subsequent procedures to correct the alignment is reduced. Moreover, the delivery device 10 is applicable to a wide range of applications, such as deploying implantable devices and surgical procedures.

Many modifications and other embodiments of the invention set forth herein will come to mind to one skilled in the art That which is claimed:

1. A delivery device for positioning and deploying an implantable device within a lumen comprising:
   a longitudinal outer tube having a proximal end and a distal end, wherein the outer tube is configured to receive the implantable device at a position within the outer tube and proximate to the distal end of the outer tube;
   a longitudinal inner tube slidably disposed within the outer tube and having a proximal end and a distal end, wherein at least a portion of the distal end of the inner tube is configured to underlie a proximal end of the implantable device about an inner circumference of the implantable device, and wherein the distal end of the inner tube is located proximally of the distal end of the outer tube to define a gap for accommodating at least a portion of the implantable device;
   a deployment mechanism coupled to at least one of the inner and outer tubes and operable to deploy the implantable device within the lumen, wherein the deployment mechanism comprises:
      a first actuator to at least partially move the outer tube proximally and longitudinally relative to the inner tube,
      a connector connected to the first actuator, and
      a second actuator positioned proximal to the first actuator and operatively connected to the first actuator via the connector to move the outer tube proximally and longitudinally relative to the inner tube,
      wherein the first actuator and the second actuator are configured to be retracted in succession to provide staged deployment of the implantable device such that retracting the second actuator moves the first actuator and the outer tube proximally and longitudinally relative to the inner tube from a first position to a second position to cause partial deployment of the implantable device and subsequent retraction of the first actuator slidably and proximally within the connector toward the second actuator moves the outer tube proximally and longitudinally relative to the inner tube from the second position to a third position to cause full deployment of the implantable device; and
   an optical device configured to be positioned within the gap to view at least a portion of an interior of the implantable device within the outer tube prior to deployment of the implantable device.

2. The delivery device according to claim 1, wherein the optical device is capable of being positioned within the gap to view at least a portion of the lumen proximate to a target deployment area.

3. The delivery device according to claim 1, wherein each of the inner and outer tubes comprises a side opening defined therein, and wherein the outer tube is capable of sliding over the inner tube to substantially align each of the side openings with one another.

4. The delivery device according to claim 1, wherein each of the inner and outer tubes comprises a coil positioned therein.

5. The delivery device according to claim 4, wherein the coil of the inner tube extends proximate to its distal end, and wherein the coil of the outer tube extends proximally of its distal end such that the coils are capable of aligning with one another prior to deploying the implantable device.

6. The delivery device according to claim 1, wherein at least one of the inner and outer tubes comprises a semi-transparent polymeric material.

7. The delivery device according to claim 6, wherein the polymeric material comprises at least one of polytetrafluoroethylene and polyether block amide.

8. The delivery device according to claim 6, wherein the outer tube comprises a semi-transparent polymeric material and the inner tube comprises a side opening defined therein, and wherein the optical instrument is capable of viewing the lumen through the side opening and the outer tube.

9. The delivery device according to claim 1, further comprising a distal portion coupled to the inner tube with a collar, wherein the distal portion is configured to underlie the proximal end of the implantable device about the inner circumference of the implantable device.

10. The delivery device according to claim 9, wherein the distal portion comprises at least one anchor extending outwardly therefrom and configured to interiorly engage at least a portion of the proximal end of the implantable device.

11. The delivery device according to claim 1, wherein the first actuator is directly coupled to the outer tube.

12. A method for deploying an implantable device within a lumen proximate to a target area comprising:
   obtaining a delivery device including an inner tube within an outer tube such that a gap is defined between respective distal ends of each of the inner and outer tubes and an implantable device positioned at least partially within the gap with at least a portion of the distal end of the inner tube interiorly within the implantable device such that the inner tube underlies the implantable device about an inner circumference thereof;
   positioning the inner and outer tubes within the lumen proximate to the target area;
   positioning an optical device within the gap to view at least a portion of at least one of the implantable device and the target area from within the outer tube prior to deployment of the implantable device;
   retracting a proximal actuator of a deployment mechanism of the delivery device, the proximal actuator operably connected via a connector to a distal actuator that is operably connected to the outer tube of the delivery device, wherein the proximal actuator and the distal actuator of the deployment device are configured to be retracted in succession to provide staged deployment of the implantable device, wherein retracting the proximal actuator moves the distal actuator and the outer tube proximally and longitudinally relative to the inner tube and thereby at least partially moves the outer tube proximally and longitudinally relative to the inner tube from a first position to a second position to cause partial deployment of the implantable device; and
   retracting the distal actuator of the deployment mechanism slidably and proximally within the connector toward the proximal actuator, subsequent to retracting the proximal actuator, to move the outer tube proximally and longitudinally relative to the inner tube, from the second position to a third position, to cause full deployment of the implantable device.

13. The method according to claim 12, wherein the implantable device is positioned over at least one anchor extending outwardly from the distal end of the inner tube such that the at least one anchor interiorly engages the implantable device.

14. The method according to claim 12, further comprising moving the inner and outer tubes proximally within the lumen while the implantable device is positioned within the gap to reposition the implantable device.

15. A delivery device for positioning and deploying an implantable device within a lumen comprising:
- a longitudinal outer tube having a proximal end and a distal end, wherein at least a portion of the implantable device is disposed in direct contact with the outer tube proximate to the distal end of the outer tube prior to deploying the implantable device;
- a shortened inner tube slidably disposed within the outer tube and having a proximal end and a distal end, wherein at least a portion of the distal end of the inner tube comprises at least one anchor extending outwardly from the inner tube and configured to interiorly engage at least a portion of a proximal end of the implantable device; and
- a deployment mechanism coupled to at least one of the inner and outer tubes and operable to deploy the implantable device within the lumen, wherein the deployment mechanism comprises:
  - a distal actuator to at least partially move the outer tube proximally and longitudinally relative to the inner tube,
  - a connector coupled to the distal actuator, and
  - a proximal actuator positioned proximal to the distal actuator and operably connected to the distal actuator via the connector to move the outer tube proximally and longitudinally relative to the inner tube,
  - wherein the distal actuator and the proximal actuator are configured to be retracted in succession to provide staged deployment of the implantable device such that retracting the proximal actuator moves the distal actuator and the outer tube proximally and longitudinally relative to the inner tube from a first position to a second position to cause partial deployment of the implantable device and subsequent retraction of the distal actuator slidably and proximally within the connector toward the proximal actuator moves the outer tube proximally and longitudinally relative to the inner tube from the second position to a third position to cause full deployment of the implantable device; and
  - an optical device configured to be positioned to view at least a portion of an interior of the implantable device within the outer tube prior to deployment of the implantable device.

16. The delivery device according to claim 15, wherein the distal end of the inner tube is located proximally of the distal end of the outer tube to define a gap for accommodating at least a portion of the implantable device.

17. The delivery device according to claim 16, wherein the optical device is configured to be positioned within the gap to view the at least a portion of the interior of the implantable device and to view at least a portion of the lumen.

18. The delivery device according to claim 15, wherein the inner tube further comprises a distal portion coupled thereto with a collar, wherein the distal portion is configured to underlie at least a portion of the proximal end of the implantable device.

19. The delivery device according to claim 18, wherein the distal portion comprises the at least one anchor.

20. The delivery device according to claim 15, wherein at least one of the inner and outer tubes comprises a semi-transparent polymeric material.

21. The delivery device according to claim 20, wherein the outer tube comprises a semi-transparent polymeric material and the inner tube comprises a side opening defined therein, and wherein an optical instrument is capable of viewing the lumen through the side opening and the outer tube.

22. The delivery device of claim 9, wherein the collar has a larger outer diameter then the inner tube.

23. The delivery device of claim 15, wherein the inner tube comprises a plurality of anchors spaced circumferentially apart from one another.

24. The delivery device of claim 15, wherein the at least one anchor comprises a protuberance extending outwardly from an outer surface of the inner tube.

25. The delivery device of claim 18, wherein the collar has a larger outer diameter than the inner tube.

26. The delivery device of claim 1, wherein the connector comprises an aperture and the second actuator is configured to slide proximally within the aperture to fully deploy the implantable device.

* * * * *